United States Patent [19]

Fogarty

[11] 4,328,811
[45] May 11, 1982

[54] CALIBRATING DILATION CATHETER

[76] Inventor: Thomas J. Fogarty, 770 Welch Rd., Palo Alto, Calif. 94304

[21] Appl. No.: 172,764

[22] Filed: Jul. 28, 1980

[51] Int. Cl.³ .............................................. A61M 29/02
[52] U.S. Cl. ................................ 128/774; 128/349 B; 128/DIG. 9
[58] Field of Search ............. 128/774, 349 B, DIG. 9, 128/348, 349 R

[56] References Cited

U.S. PATENT DOCUMENTS

| 3,692,018 | 9/1972 | Goetz | 128/344 |
| 3,848,602 | 11/1974 | Gutnick | 128/349 B |
| 4,020,829 | 5/1977 | Willson | 128/DIG. 9 |
| 4,271,839 | 6/1981 | Fogarty et al. | 128/349 B |

Primary Examiner—Lee S. Cohen
Assistant Examiner—Daniel P. Burke
Attorney, Agent, or Firm—Naylor, Neal & Uilkema

[57] ABSTRACT

A catheter is provided with an inflatable-deflatable balloon element to radially enlarge a partially occluded artery lumen and the catheter is provided with a calibrator oval to internally gauge the enlarged lumen.

4 Claims, 6 Drawing Figures

CALIBRATING DILATION CATHETER

RELATED APPLICATIONS

Co-pending application Ser. No. 060,408, filed July 25, 1979, now U.S. Pat. No. 4,271,839 for Dilatation Catheter Method and Apparatus shows a dilatation catheter in which dilatation is accomplished by everting a balloon from the end of a catheter, blowing the balloon up to dilate an occluded blood vessel, deflating the balloon, and re-inverting the balloon within the catheter.

Co-pending application Ser. No. 114,979 filed Jan. 24, 1980 for Flexible Calibrator shows a catheter having a calibrator bead at the distal end thereof which is used to measure the diameter of the lumen in a stenotic segment of blood vessel. The present invention comprises a calibrator bead in trailing relation to a dilatation balloon. The combination of these two elements enables the calibrator element to measure the lumen of the dilated artery rather than, as in the co-pending application, being used to measure the lumen of an occluded passage in a pre-dilated artery.

BACKGROUND OF THE INVENTION

The present invention relates to a method and apparatus for use in dilating occluded blood vessels and for measuring the degree of dilation of the occlusions within these vessels. Prior to the present invention these two objectives were attainable, as a result of the teachings set forth in the above-identified copending patent applications, by the use of two catheters, one having a balloon element to dilate the occlusion and the other having a calibrator element to measure the widened lumen of the occluded segment of artery. This could result in the repeated insertion and removal of catheters into and out of arteries until the sizes of the enlarged passages of the occluded segments of the arteries were of acceptable dimensions. The heavier the traffic of catheters within blood vessels the greater is the risk that material may be accidentally dislodged therefrom with possible consequent blockage elsewhere in the blood circulation system.

SUMMARY OF THE INVENTION

The present invention combines in a single catheter a dilatation balloon element and a calibrator bead element. Following dilatation of an occlusion the calibrator bead may be moved into the dilated lumen of the occlusion in order to determine whether the occlusion has been sufficiently dilated. The two objects are thereby achieved without the need of indulging in the time-consuming and hazardous activities of repeatedly removing and replacing catheters.

The principal object of the invention is to combine in a single catheter instrument dilatation balloon means which can be inflated and deflated and calibrator bead means to measure the lumen of the dilated occlusion in the artery.

This and other objects and advantages of the invention will be apparent from the following description taken in conjunction with the drawings forming part of this specification.

DESCRIPTION OF THE PREFERRED EMBODIMENT

Figure 1:
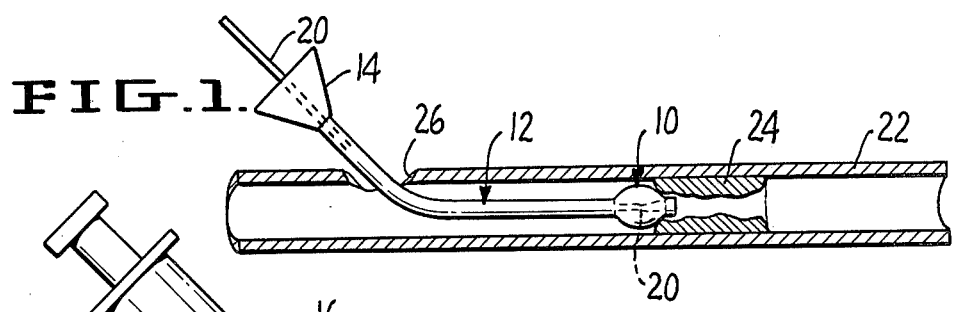
FIG. 1 is a semi-schematic view of the present catheter positioned adjacent an occlusion.
Figure 2:
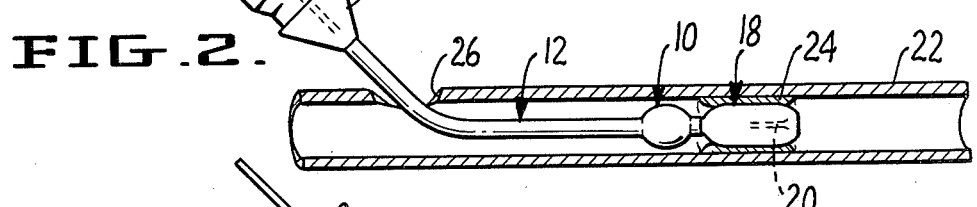
FIG. 2 is a similar view showing the occlusion being dilated.
Figure 3:
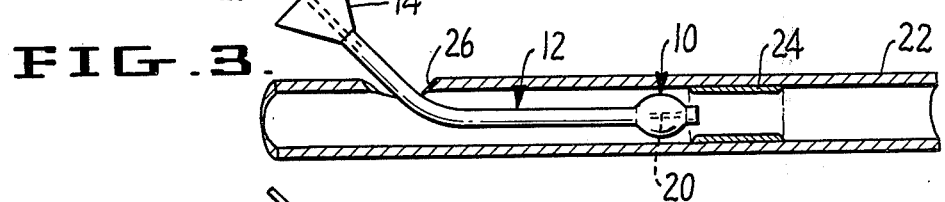
FIG. 3 is a similar view showing the balloon element reinverted.

The catheter comprises a calibrator oval 10, a flexible shaft 12, a manifold 14 which serves for the connection of a syringe 16 to the instrument, a balloon 18 which is longitudinally extensible from the oval 10 under the fluid pressure applied by syringe 16 and thereafter laterally expansible under increased fluid pressure, and a guide wire 20 to be pulled to re-invert the balloon 18 within the oval 10.

Figure 4:
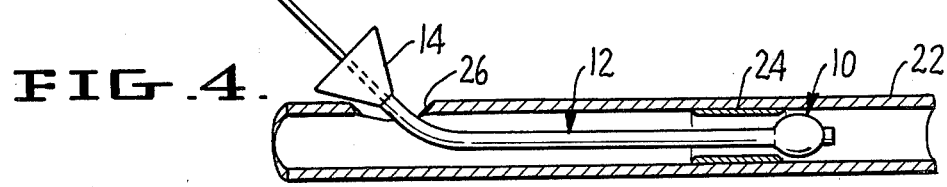
FIG. 4 is a similar view showing the catheter during the course of movement through the same artery to the next occlusion to be treated.

A blood vessel 22 partially occluded by occlusion 24 is provided with an incision 26 for the introduction into the vessel of the catheter. The catheter is moved along the vessel until the oval 10 bears against the end of occlusion 24, as shown in FIG. 1. The syringe 16 is then attached to manifold 14 and actuated to evert the balloon 18 and extend it into the restricted lumen of occlusion 24. The fluid pressure is then increased to radially expand the balloon and compress the occlusion. The fluid pressure is then reduced by reverse operation of the syringe and the syringe is removed from manifold 14. Wire 20 is then manually pulled to re-invert the balloon within the oval. The oval is then moved within the compressed occlusion 24. Ready movability of the oval through the occlusion indicates that the occlusion has been adequately compressed. If the oval is not readily movable through the occlusion the instrument is used to further compress the occlusion. Once the occlusion has been suitably compressed the instrument may be moved further along the vessel 22, as indicated in FIG. 4, if there is a further occlusion to be treated.

Figure 5:
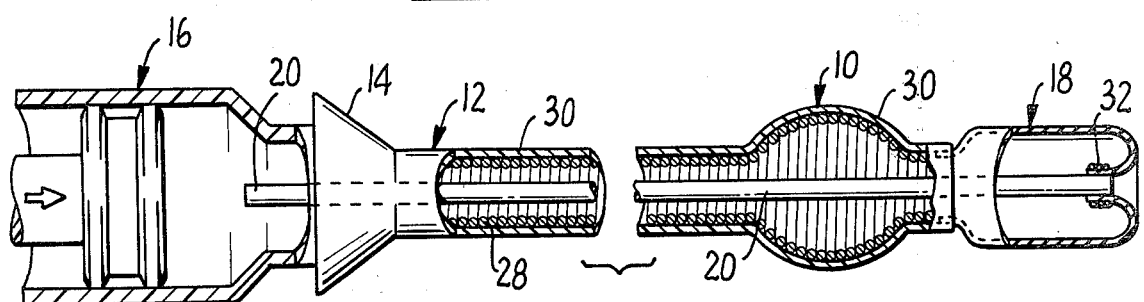
FIG. 5 is a view showing in elevation and longitudinal cross-section the details and construction of the present catheter with the balloon element everted.
Figure 6:
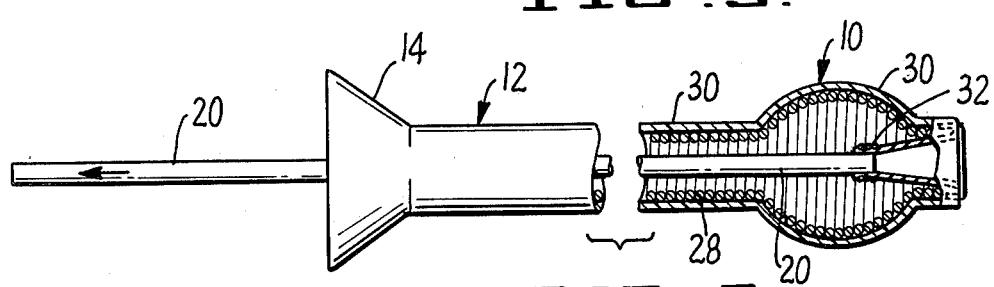
FIG. 6 is a view like that of FIG. 5 showing the balloon element in inverted condition.

The details of construction of the instrument are shown in FIGS. 5–6. The oval 10 and shaft 12 are formed by a tightly wound helical spring 28 which provides the catheter with sufficient flexibility to enable its movement through tortuous arteries. The oval and shaft are provided with an overcoating 30 of silicone, heat-shrink tubing, Teflon, or the like.

The balloon element 18 is made of an elastomeric material such as latex. One end of the balloon is attached to the end of the oval 10 and the other end of the balloon is attached with suture 32 to guide wire 20. The wire 20 is small in diameter relative to the internal diameter of spring 28 to provide an annular fluid passage between the syringe 16 and balloon 18.

Expansion of the balloon element out of the end of the catheter takes place in anisotropic fashion, with the balloon element first everting out of the catheter in advance of substantial lateral expansion, and then, after eversion, laterally expanding in response to the continued exertion of fluid pressure internally of the catheter. Optimal dimensional data for the catheter and the balloon element are set forth in my co-pending application Ser. No. 060,408.

While the invert-evert form of balloon is preferred, other types and forms of balloons may be used as long as they do not impede the movability of the catheters through the arteries and as long as they do not interfere with the use of the calibrator ovals to measure or calibrate the inside diameters of the arterial lumens.

What is claimed is:

1. A catheter for dilating a partially occluded section of a blood vessel and for calibrating the internal diameter of the dilated section, said catheter comprising a flexible hollow shaft, laterally expansible and retractable balloon means carried by said shaft at the distal end thereof, and an enlarged and normally incompressible calibrator oval of a predetermined diameter carried by said shaft in adjacent relation to the proximal end of said balloon means for the calibration of the internal diameter of said occluded section after said section has been dilated by lateral expansion of said balloon means and said balloon means has been laterally retracted.

2. The catheter of claim 1, said oval having a passageway extending longitudinally therethrough, said passageway constituting a means for transmitting a pressurizing fluid to and from said balloon means and constituting a means for storing said balloon means in inverted condition within said oval, said balloon means being evertable from said oval by pressurizing fluid applied internally thereto along said shaft and oval.

3. The catheter of claim 2, said balloon means having attached to the distal end thereof a flexible guide wire which extends through said oval and shaft and from the proximal end of the catheter, said balloon means being re-invertable within said oval by the pulling of said wire.

4. The cathether of claim 2, said shaft and said oval being formed of a tightly wound helical spring.

* * * * *